United States Patent
Mower

(10) Patent No.: US 7,908,003 B1
(45) Date of Patent: Mar. 15, 2011

(54) SYSTEM AND METHOD FOR TREATING ISCHEMIA BY IMPROVING CARDIAC EFFICIENCY

(75) Inventor: Morton M. Mower, Baltimore, MD (US)

(73) Assignee: MR3 Medical LLC, North Oaks, MN (US)

( * ) Notice: Subject to any disclaimer, the term of this patent is extended or adjusted under 35 U.S.C. 154(b) by 652 days.

(21) Appl. No.: 11/763,768

(22) Filed: Jun. 15, 2007

Related U.S. Application Data

(63) Continuation-in-part of application No. 11/731,203, filed on Mar. 30, 2007, which is a continuation of application No. 10/754,887, filed on Jan. 10, 2004, now Pat. No. 7,203,537, which is a continuation-in-part of application No. 09/929,478, filed on Aug. 14, 2001, now Pat. No. 6,895,274, which is a continuation of application No. 09/231,570, filed on Jan. 14, 1999, now Pat. No. 6,295,470, which is a continuation-in-part of application No. 08/699,552, filed on Aug. 19, 1996, now Pat. No. 5,871,506.

(60) Provisional application No. 60/814,734, filed on Jun. 19, 2006.

(51) Int. Cl.
*A61N 1/00* (2006.01)
(52) U.S. Cl. .............................................. 607/9; 607/22
(58) Field of Classification Search .................. 607/4–28
See application file for complete search history.

(56) References Cited

U.S. PATENT DOCUMENTS

| | | | |
|---|---|---|---|
| 3,572,345 | A | 3/1971 | Auphan |
| 3,587,567 | A | 6/1971 | Schiff |
| 3,651,805 | A | 3/1972 | Breiling |
| 3,651,806 | A | 3/1972 | Hirshberg |
| 3,924,641 | A | 12/1975 | Weiss |
| 3,933,147 | A | 1/1976 | Du Vall et al. |
| 3,942,536 | A | 3/1976 | Mirowski et al. |
| 3,946,745 | A | 3/1976 | Siang-Lai et al. |
| 3,952,750 | A | 4/1976 | Mirowski et al. |
| 4,010,758 | A | 3/1977 | Rockland et al. |
| 4,019,519 | A | 4/1977 | Geerling |
| 4,030,509 | A | 6/1977 | Hellman et al. |
| 4,055,190 | A | 10/1977 | Tany |
| 4,106,494 | A | 8/1978 | McEachern |
| 4,184,493 | A | 1/1980 | Langer et al. |
| 4,202,340 | A | 5/1980 | Langer et al. |
| 4,222,386 | A | 9/1980 | Smolnikov et al. |

(Continued)

FOREIGN PATENT DOCUMENTS

EP     0 314 078     5/1989

(Continued)

OTHER PUBLICATIONS

"Myofilaments: The End Effector of E-C Coupling," Chapter 2.

(Continued)

*Primary Examiner* — Scott M Getzow
(74) *Attorney, Agent, or Firm* — The Marbury Law Group PLLC

(57) ABSTRACT

A system and method for treating ischemic heart disease by increasing heart efficiency. By application of an anodal pulse at or above threshold, the efficiency of the heart is improved by increasing the resting membrane potential of the myocardial cells, increasing the size of the anodal virtual stimulatory electrode, or reducing the ventricular stretching during filling of the ventricle.

11 Claims, 6 Drawing Sheets

U.S. PATENT DOCUMENTS

| | | | |
|---|---|---|---|
| 4,223,678 A | 9/1980 | Langer et al. | |
| 4,233,986 A | 11/1980 | Tannenbaum | |
| 4,237,895 A | 12/1980 | Johnson | |
| 4,273,114 A | 6/1981 | Barkalow et al. | |
| 4,298,007 A | 11/1981 | Wright et al. | |
| 4,312,354 A | 1/1982 | Walters | |
| 4,316,472 A | 2/1982 | Mirowsky et al. | |
| 4,327,322 A | 4/1982 | Yukl | |
| 4,337,776 A | 7/1982 | Daly et al. | |
| 4,343,312 A | 8/1982 | Cals et al. | |
| 4,384,585 A | 5/1983 | Zipes | |
| 4,387,717 A | 6/1983 | Brownlee et al. | |
| 4,392,496 A | 7/1983 | Stanton | |
| 4,402,322 A * | 9/1983 | Duggan | 607/9 |
| 4,403,614 A | 9/1983 | Engle et al. | |
| 4,407,288 A | 10/1983 | Langer et al. | |
| 4,411,268 A | 10/1983 | Cox | |
| 4,429,697 A | 2/1984 | Nappholz et al. | |
| 4,440,172 A | 4/1984 | Langer | |
| 4,444,195 A | 4/1984 | Gold | |
| 4,456,012 A | 6/1984 | Lattin | |
| 4,481,953 A | 11/1984 | Gold et al. | |
| 4,498,478 A | 2/1985 | Bourgeois | |
| 4,503,857 A | 3/1985 | Boute et al. | |
| 4,539,991 A | 9/1985 | Boute et al. | |
| 4,543,956 A | 10/1985 | Herscovici | |
| 4,554,922 A | 11/1985 | Prystowsky et al. | |
| 4,559,946 A | 12/1985 | Mower | |
| 4,566,456 A | 1/1986 | Koning et al. | |
| 4,569,350 A | 2/1986 | Mumford et al. | |
| 4,572,191 A | 2/1986 | Mirowski et al. | |
| RE32,091 E | 3/1986 | Stanton | |
| 4,612,934 A | 9/1986 | Borkan | |
| 4,628,934 A | 12/1986 | Pohndorf et al. | |
| 4,637,397 A | 1/1987 | Jones et al. | |
| 4,646,744 A | 3/1987 | Capel | |
| 4,651,716 A | 3/1987 | Forester et al. | |
| 4,662,377 A | 5/1987 | Heilman et al. | |
| 4,674,508 A | 6/1987 | DeCote | |
| 4,679,572 A | 7/1987 | Baker, Jr. | |
| 4,690,155 A | 9/1987 | Hess | |
| 4,723,552 A | 2/1988 | Kenyon et al. | |
| 4,726,379 A | 2/1988 | Altman et al. | |
| 4,729,376 A | 3/1988 | DeCote, Jr. | |
| 4,754,759 A | 7/1988 | Allocca | |
| 4,765,341 A | 8/1988 | Mower et al. | |
| 4,781,194 A | 11/1988 | Elmqvist | |
| 4,821,724 A | 4/1989 | Whigham et al. | |
| 4,823,810 A | 4/1989 | Dervieux | |
| 4,830,006 A | 5/1989 | Haluska et al. | |
| 4,875,484 A | 10/1989 | Anzai et al. | |
| 4,903,700 A | 2/1990 | Whigham et al. | |
| 4,919,140 A | 4/1990 | Borgens et al. | |
| 4,924,880 A | 5/1990 | O'Neill et al. | |
| 4,928,688 A | 5/1990 | Mower | |
| 4,940,054 A | 7/1990 | Grevis et al. | |
| 4,944,298 A | 7/1990 | Sholder | |
| 4,976,264 A | 12/1990 | Petrofsky | |
| 4,979,507 A | 12/1990 | Heinz et al. | |
| 4,989,605 A | 2/1991 | Rossen | |
| 4,996,987 A | 3/1991 | Petrofsky | |
| 4,998,531 A | 3/1991 | Bocchi et al. | |
| 5,002,052 A | 3/1991 | Haluska | |
| 5,003,976 A | 4/1991 | Alt | |
| 5,018,522 A | 5/1991 | Mehra | |
| 5,020,544 A | 6/1991 | Dahl et al. | |
| 5,022,396 A | 6/1991 | Wantanabe | |
| 5,026,397 A | 6/1991 | Aoki et al. | |
| 5,027,815 A | 7/1991 | Funke et al. | |
| 5,036,850 A | 8/1991 | Owens | |
| 5,044,375 A | 9/1991 | Bach, Jr. et al. | |
| 5,048,522 A | 9/1991 | Petrofsky | |
| 5,052,391 A | 10/1991 | Silberstone et al. | |
| 5,058,584 A | 10/1991 | Bourgeois | |
| 5,063,929 A | 11/1991 | Bartelt et al. | |
| 5,065,083 A | 11/1991 | Owens | |
| 5,069,211 A | 12/1991 | Bartelt et al. | |
| 5,083,564 A | 1/1992 | Scherlag | |
| 5,085,218 A | 2/1992 | Heil, Jr. et al. | |
| 5,087,243 A | 2/1992 | Avitall | |
| 5,097,832 A | 3/1992 | Buchanan | |
| 5,097,833 A | 3/1992 | Campos | |
| 5,105,810 A | 4/1992 | Collins et al. | |
| 5,109,847 A | 5/1992 | Liss et al. | |
| 5,111,811 A | 5/1992 | Smits | |
| 5,111,815 A | 5/1992 | Mower | |
| 5,117,826 A | 6/1992 | Bartelt et al. | |
| 5,129,394 A | 7/1992 | Mehra | |
| 5,156,147 A | 10/1992 | Warren et al. | |
| 5,156,149 A | 10/1992 | Hudrlik | |
| 5,161,527 A | 11/1992 | Nappholz et al. | |
| 5,163,428 A | 11/1992 | Pless | |
| 5,163,429 A | 11/1992 | Cohen | |
| 5,181,511 A | 1/1993 | Nickolls et al. | |
| 5,188,106 A | 2/1993 | Nappholz et al. | |
| 5,193,535 A | 3/1993 | Bardy et al. | |
| 5,193,536 A | 3/1993 | Mehra | |
| 5,199,428 A * | 4/1993 | Obel et al. | 607/44 |
| 5,205,284 A | 4/1993 | Freeman | |
| 5,209,229 A | 5/1993 | Gilli | |
| 5,213,098 A | 5/1993 | Bennett et al. | |
| 5,215,083 A | 6/1993 | Drane et al. | |
| 5,224,475 A | 7/1993 | Berg et al. | |
| 5,224,476 A | 7/1993 | Ideker et al. | |
| 5,233,985 A | 8/1993 | Hudrlik | |
| 5,236,413 A | 8/1993 | Feiring | |
| 5,282,785 A | 2/1994 | Shapland et al. | |
| 5,284,491 A | 2/1994 | Sutton et al. | |
| 5,286,254 A | 2/1994 | Shapland et al. | |
| 5,292,340 A | 3/1994 | Crosby et al. | |
| 5,300,096 A | 4/1994 | Hall et al. | |
| 5,305,745 A | 4/1994 | Zacouto | |
| 5,314,423 A | 5/1994 | Seney | |
| 5,314,495 A | 5/1994 | Kovacs | |
| 5,318,591 A | 6/1994 | Causey, III et al. | |
| 5,320,642 A | 6/1994 | Sherlag | |
| 5,320,643 A | 6/1994 | Roline et al. | |
| 5,324,327 A | 6/1994 | Cohen | |
| 5,327,887 A | 7/1994 | Nowakoski | |
| 5,332,401 A | 7/1994 | Davey et al. | |
| 5,334,220 A | 8/1994 | Sholder | |
| 5,340,361 A | 8/1994 | Sholder | |
| 5,346,506 A | 9/1994 | Mower et al. | |
| 5,350,401 A | 9/1994 | Levine | |
| 5,353,800 A | 10/1994 | Pohndorf et al. | |
| 5,366,486 A | 11/1994 | Zipes et al. | |
| 5,368,040 A | 11/1994 | Carney | |
| 5,370,665 A | 12/1994 | Hudrlik | |
| 5,386,837 A | 2/1995 | Sterzer | |
| 5,387,419 A | 2/1995 | Levy et al. | |
| 5,391,185 A | 2/1995 | Kroll | |
| 5,391,192 A | 2/1995 | Lu et al. | |
| 5,391,199 A | 2/1995 | Ben-Haim | |
| 5,411,525 A | 5/1995 | Swanson et al. | |
| 5,411,547 A | 5/1995 | Causey, III | |
| 5,415,629 A | 5/1995 | Henley | |
| 5,417,717 A | 5/1995 | Salo et al. | |
| 5,417,718 A | 5/1995 | Kleks et al. | |
| 5,419,763 A | 5/1995 | Hildebrand | |
| 5,421,830 A | 6/1995 | Epstein et al. | |
| 5,422,525 A | 6/1995 | Mansir | |
| 5,423,868 A | 6/1995 | Nappholz et al. | |
| 5,431,688 A | 7/1995 | Freeman | |
| 5,433,730 A | 7/1995 | Alt | |
| 5,441,522 A | 8/1995 | Schuller | |
| 5,443,485 A | 8/1995 | Housworth et al. | |
| 5,445,609 A | 8/1995 | Lattin et al. | |
| 5,447,520 A | 9/1995 | Spano | |
| 5,447,525 A | 9/1995 | Powell et al. | |
| 5,458,568 A | 10/1995 | Racchini et al. | |
| 5,458,619 A | 10/1995 | Olson | |
| 5,458,625 A | 10/1995 | Kendall | |
| 5,464,020 A | 11/1995 | Lerner | |
| 5,468,254 A | 11/1995 | Hahn et al. | |
| 5,472,453 A | 12/1995 | Alt | |
| 5,476,484 A | 12/1995 | Hedberg | |
| 5,476,485 A | 12/1995 | Weinberg et al. | |

| | | |
|---|---|---|
| 5,480,413 A | 1/1996 | Greenhut et al. |
| 5,487,759 A | 1/1996 | Bastyr et al. |
| 5,499,971 A | 3/1996 | Shapland et al. |
| 5,501,662 A | 3/1996 | Hofmann |
| 5,507,781 A | 4/1996 | Kroll et al. |
| 5,514,161 A | 5/1996 | Limousin |
| 5,514,162 A | 5/1996 | Bornzin et al. |
| 5,514,163 A | 5/1996 | Markowitz et al. |
| 5,522,858 A | 6/1996 | van der Veen |
| 5,527,347 A | 6/1996 | Shelton et al. |
| 5,531,764 A | 7/1996 | Adams et al. |
| 5,534,015 A | 7/1996 | Kroll et al. |
| 5,534,018 A | 7/1996 | Wahlstrand et al. |
| 5,540,722 A | 7/1996 | Clare et al. |
| 5,540,730 A | 7/1996 | Terry et al. |
| 5,545,186 A | 8/1996 | Olson et al. |
| 5,549,652 A | 8/1996 | McClure et al. |
| 5,556,421 A | 9/1996 | Prutchi et al. |
| 5,562,708 A | 10/1996 | Combs et al. |
| 5,568,809 A | 10/1996 | Ben-Haim |
| 5,571,143 A | 11/1996 | Hoegnelid et al. |
| 5,584,803 A | 12/1996 | Stevens et al. |
| 5,584,868 A | 12/1996 | Salo et al. |
| 5,601,608 A | 2/1997 | Mouchawar |
| 5,601,609 A | 2/1997 | Duncan |
| 5,601,611 A | 2/1997 | Fayram et al. |
| 5,601,615 A | 2/1997 | Markowitz et al. |
| 5,620,468 A | 4/1997 | Mongeon et al. |
| 5,620,470 A | 4/1997 | Gliner et al. |
| 5,620,471 A | 4/1997 | Duncan |
| 5,626,620 A | 5/1997 | Kieval et al. |
| 5,626,622 A | 5/1997 | Cooper |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,651,379 A | 7/1997 | Matheny et al. |
| 5,658,319 A | 8/1997 | Kroll |
| 5,662,698 A | 9/1997 | Altman et al. |
| 5,674,251 A | 10/1997 | Combs et al. |
| 5,674,253 A | 10/1997 | Adams et al. |
| 5,674,259 A | 10/1997 | Gray |
| 5,683,429 A | 11/1997 | Mehra |
| 5,683,431 A | 11/1997 | Wang |
| 5,690,691 A | 11/1997 | Chen et al. |
| 5,693,952 A | 12/1997 | Cox |
| 5,697,953 A | 12/1997 | Kroll et al. |
| 5,713,924 A | 2/1998 | Min et al. |
| 5,713,929 A | 2/1998 | Hess et al. |
| 5,713,935 A | 2/1998 | Prutchi et al. |
| 5,718,720 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,303 A | 4/1998 | Kroll et al. |
| 5,749,906 A | 5/1998 | Kieval |
| 5,755,740 A | 5/1998 | Nappholz |
| 5,766,225 A | 6/1998 | Kramm |
| 5,782,876 A | 7/1998 | Flammang |
| 5,782,881 A | 7/1998 | Lu et al. |
| 5,792,198 A | 8/1998 | Nappholz |
| 5,797,967 A | 8/1998 | Gray |
| 5,800,464 A | 9/1998 | Kieval |
| 5,800,465 A | 9/1998 | Thompson et al. |
| 5,807,234 A | 9/1998 | Bui et al. |
| 5,814,079 A | 9/1998 | Kieval |
| 5,814,086 A | 9/1998 | Hirchberg |
| 5,824,017 A | 10/1998 | Sullivan |
| 5,836,994 A | 11/1998 | Bourgeois |
| 5,855,592 A | 1/1999 | McGee et al. |
| 5,855,594 A | 1/1999 | Olive et al. |
| 5,871,506 A | 2/1999 | Mower |
| 5,871,560 A | 2/1999 | Mower |
| 5,876,422 A | 3/1999 | van Groeningen |
| 5,968,081 A | 10/1999 | Levine |
| 6,026,326 A | 2/2000 | Bardy |
| 6,067,470 A | 5/2000 | Mower |
| 6,136,019 A | 10/2000 | Mower |
| 6,141,586 A | 10/2000 | Mower |
| 6,141,587 A | 10/2000 | Mower |
| 6,178,351 B1 | 1/2001 | Mower |
| 6,216,039 B1 | 4/2001 | Bourgeois |
| 6,223,072 B1 | 4/2001 | Mika et al. |
| 6,248,126 B1 | 6/2001 | Lesser et al. |
| 6,263,242 B1 | 7/2001 | Mika et al. |
| 6,292,693 B1 | 9/2001 | Darvish et al. |
| 6,317,631 B1 | 11/2001 | Ben-Haim et al. |
| 6,360,126 B1 | 3/2002 | Mika et al. |
| 6,363,279 B1 | 3/2002 | Ben-Haim et al. |
| 6,370,430 B1 | 4/2002 | Mika et al. |
| 6,381,493 B1 * | 4/2002 | Stadler et al. ................ 607/9 |
| 6,424,866 B2 | 7/2002 | Mika et al. |
| 6,571,127 B1 | 5/2003 | Ben-Haim et al. |
| 6,597,952 B1 | 7/2003 | Mika et al. |
| 6,689,288 B2 | 2/2004 | St. Clair et al. |
| 6,947,792 B2 | 9/2005 | Ben-Haim et al. |
| 7,020,530 B1 * | 3/2006 | Ideker et al. ................ 607/122 |
| 2003/0014097 A1 | 1/2003 | Putz et al. |
| 2004/0158289 A1 | 8/2004 | Girouard et al. |

FOREIGN PATENT DOCUMENTS

| | | |
|---|---|---|
| EP | A-538990 | 4/1993 |
| EP | 0 727 241 A1 | 8/1996 |
| EP | 0 491 649 | 9/1996 |
| EP | 0 813 889 | 12/1997 |
| EP | 0 850 662 | 7/1998 |
| EP | 0 870 516 | 10/1998 |
| EP | 0 600 631 | 12/1999 |
| FR | 2763247 | 5/1997 |
| JP | S62-275471 | 11/1987 |
| JP | A-63-229069 | 9/1988 |
| JP | A-5-345034 | 12/1993 |
| JP | T-5-508574 | 12/1993 |
| JP | A-8-243176 | 9/1996 |
| JP | A-9-103502 | 4/1997 |
| JP | A-10-24109 | 1/1998 |
| JP | A-10-57509 | 3/1998 |
| JP | A-2000-506034 | 5/2000 |
| JP | A-2001-519216 | 10/2001 |
| JP | A-2001-522272 | 11/2001 |
| WO | WO 92/00716 | 1/1992 |
| WO | WO 93/01861 | 2/1993 |
| WO | WO 93/18820 | 9/1993 |
| WO | WO 94/17855 | 8/1994 |
| WO | WO 95/08316 | 3/1995 |
| WO | WO 96/16696 | 6/1996 |
| WO | WO 97/13547 | 4/1997 |
| WO | WO-97/22382 | 6/1997 |
| WO | WO 97/25098 | 7/1997 |
| WO | WO 97/25101 | 7/1997 |
| WO | WO 97/41922 | 11/1997 |
| WO | WO 98/10828 | 3/1998 |
| WO | WO 98/10829 | 3/1998 |
| WO | WO 98/10830 | 3/1998 |
| WO | WO 98/10832 | 3/1998 |
| WO | WO 98/10831 | 4/1998 |
| WO | WO 98/19719 | 5/1998 |
| WO | WO-98/39060 | 9/1998 |
| WO | WO 98/40122 | 9/1998 |
| WO | WO 99/03533 | 1/1999 |
| WO | WO 99/09971 | 3/1999 |
| WO | WO 99/36124 | 7/1999 |
| WO | WO-99/61100 | 12/1999 |
| WO | WO 99/61101 | 12/1999 |
| WO | WO 00/01443 | 1/2000 |
| WO | WO 00/27475 | 5/2000 |
| WO | WO 00/42914 | 7/2000 |
| WO | WO 00/53257 | 9/2000 |
| WO | WO 00/74773 A1 | 12/2000 |
| WO | WO 01/49367 A1 | 7/2001 |
| WO | WO 01/52931 A1 | 7/2001 |
| WO | WO 01/66183 A1 | 9/2001 |
| WO | WO 01/91854 A1 | 12/2001 |
| WO | WO 01/93950 A1 | 12/2001 |
| WO | WO 01/93951 A1 | 12/2001 |

OTHER PUBLICATIONS

Allen M. Greenspan, M.D., "Electrophysiology of Pacing," 29-35, Ideal Cardiac Pacing, vol. 37 in the Series, Major Problems in Clinical Surgery (1984).

Antoni, H., et al., "Polarization Effects of Sinusoidal 50-Cycle Alternating Current on Membrane Potential of Mammalian Cardiac Fibres," Pflugers Arch. 314, 274-291 (1970).

Bakker, Patricia F., M.D., et al., "Beneficial Effects of Biventricular Pacing in Congestive Heart Failure,".

Bakker, Patricia, M.D., et al., "Biventricular Pacing Improves Functional Capacity in Patients with End-stage Congestive Heart Failure," 825, pt. II (Apr. 1995).

Bargheer, K., et al., "Prolongation of monophasic action potential duration and the refractory period in the human heart by tedisamil, a new potassium-blocking agent," The European Society of Cardiology (1994) (Copyright 1994 The European Society of Cardiology).

Bradley J. Roth, Ph.D., "Strength-Internal Curves for Cardiac Tissue Predicted Using the Bidomain Model," Journal of Cardiovascular Electrophysiology, vol. 7, No. 8, 722-737 (Aug. 1996).

Brian F. Hoffman, M.D., and Paul F. Cranefield, M.D., Electrophysiology of the Heart, 220-222, (1976).

Brian G. Cleland, "A Conceptual Basis for Pacing Waveforms," Pace, vol. 19, 1177-1185 (Aug. 1996).

Burfeind, William R., Jr., et al., "The effects of mechanical cardiac stabilization on left ventricular performance," European Journal of Cardio-thoracic Surgery 14, 285-289 (1998) (Copyright 1998 Elsevier Science B. V.).

Cazeau, S., et al., "Multisite Pacing for End-Stage Heart Failure: Early Experience," PACE, vol. 19, pt. II, 1748-1757 (Nov. 1996).

Cheng, H., et al., "Calcium Sparks: Elementary Events Underlying Excitation-Contraction Coupling in Heart Muscle," Science, vol. 262, 740 (Oct. 29, 1993).

Cooper, M. Wayne, M.D., "Postextrasystolic Potentiation, Do We Really Know What It Means and How to Use It?" Circulation, 88:2962-2971 (1993).

Coulton, L. A., and Barker, A. T., "Magnetic fields and intracellular calcium: effects on lymphocytes exposed to conditions for 'cyclotron resonance,'" Phys. Med. Biol., 38:347-360 (1993).

Devedeux, Dominique, M.S., et al., "Uterine electromyography: A critical review," Am J Obstet Gynecol., 169:1636-53 (1993) (Copyright 1993 Mosby-Year Book, Inc.).

Dillon, Stephen M., "Optical Recordings in the Rabbit Heart Show That Defibrillation Strength Shocks Prolong the Duration of Depolarization and the Refractory Period," Circulation Research, 69:842-856 (1991).

Erol-Yilmaz, A., et al., "Reversed remodeling of dilated left sided cardiomyopathy after upgrading from VVIR to VVIR biventricular pacing," Europace 4, 445-449 (2002) (Copyright 2002 Elsevier Science Ltd. on behalf of the European Society of Cardiology).

Estes et al., Implantable Cardioverter-Defibrillators, p. 181 (1994).

Euler De, Scanlon PJ. "Acetylcholine Release by a Stimulus Train Lowers Atrial Fibrillation Threshold," AM J Physiol. Oct. 1987;253(4 pt 2):H863-8.

Fain, Eric S., M.D., et al., "Improved internal defibrillation efficacy with a biphasic waveform," Am Heart J, 117:358 (1989).

Fleg, Jerome L., et al. "Impact of age on the cardiovascular response to dynamic upright exercise in healthy men and women," J Appl. Physiol. 78(3), 890-900 (1995).

Foster, Andrew H., M.D., et al., "Acute Hemodynamic Effects of Atrio-Biventricular Pacing in Humans," Am Thorac Surg, 59:294-300 (1995) (Copyright 1995 The Society of Thoracic Surgeons).

Franz, Michael R., "Method and Theory of Monophasic Action Potential Recording," Progress in Cardiovascular Diseases, vol. XXXIII, No. 6, 347-368 (May/Jun. 1991).

Franz, Michael R., M.D., Ph.D., FACC, "Bridging the Gap Between Basic and Clinical Electrophysiology: What Can Be Learned From Monophasic Action Potential Recordings?" J Cardiovasc Electrophysiol., vol. 5, No. 8, 699-710 (Aug. 1994) (Copyright 1994 Futura Publishing Company, Inc.)

Fromer, Martin, M.D., et al., "Ultrarapid Subthreshold Stimulation for Termination of Atrioventricular Node Reentrant Tachycardia," J Am Coll Cardiol., 20:879-83 (1992) (Copyright 1992 American College of Cardiology).

Fu, Ping, and Bardakjian, Berj L., "System Identification of Electrically Coupled Smooth Muscle Cells: The Passive Electrical Properties," IEEE Transactions on Biomedical Engineering, vol. 38, No. 11 (Nov. 1991) (Copyright 1991 IEEE).

Gill, Robert M., et al., "Refractory Period Extension During Ventricular Pacing at Fibrillatory Pacing Rates," PACE, vol. 20, pt. I, 647 (Mar. 1997).

Gomis, A., et al., "Oscillatory patterns of electrical activity in mouse pancreatic islets of Langerhans recorded in vivo," Pflugers Arch.—Eur. J. Physiol., 432: 510-515 (1996).

Guyton, Textbook of Medical Physiology, 8th Edition, Chapter 9, pp. 98-99, 1991.

Hakki, "Ideal Cardiac Pacing", Major Problems in Clinical Surgery, vol. 31, 1984, pp. 29-35.

Harold Siddons and Edgar Sowton, "Cardiac Pacemakers," 152-154.

Hoffman, B. F., et al., "Effects of Postextrasystolic Potentiation on Normal and Failing Hearts," Bull. N.Y. Acad. Med., 498 (Jan. 3, 1965).

Horner, S. M., et al., "Electrode for recording direction of activation, conduction velocity, and monophasic action potential of myocardium," Am J Physiol. 272, H1917-H1927 (1997) (Copyright 1997 American Physiological Society).

Inoue H, Saihara S, Toda I, Sugimoto T., "Summation and Inhibition by Ultrarapid Train Pulses in Dogs: Effects of Frequency and Duration of Trains, Lidocaine, and Beta Blockade," Pacing Clin Electrophysiol. Nov. 1989;12(11):1777-86.

Jaremko, Jacob, BSC, and Otto Rorstad, M.D., Ph.D., "Advances Toward the Implantable Artificial Pancreas for Treatment of Diabetes," Diabetes Care, vol. 21, No. 3, 444 (Mar. 1998).

Khaykin, Yaariv; Saad, Eduardo B.; Wilkoff, Bruce L. "Pacing in heart failure: The benefit of resynchronization." Cleveland Clinic Journal of Medicine, Oct. 2003, pp. 841-865, vol. 70 No. 10.

King, A. J. and D. E. M. Taylor, "The Inotropic Action of Paired Pulse Stimulation in the Normal and Failing Heart: an Experimental Study," Cardiovasc. Res., 2:122-129 (1968).

Knisley, Stephen B., et al., "Effect of Field Stimulation on Cellular Repolarization in Rabbit Myocardium, Implications for Reentry Induction," Circulation Research, 70:707-715 (1992).

Knisley, Stephen B., et al., "Prolongation and shortening of action potentials by electrical shocks in frog ventricular muscle," Am J Physiol., 6:H2348-H2358 (1994).

Koller, Bettina S., M.D., et al., "Relation Between Repolarization and Refractoriness During Programmed Electrical Stimulation in the Human Right Ventricle, Implications for Ventricular Tachycardia Induction," Circulation, 91:2378-2384 (1995) (Copyright 1995 American Heart Association, Inc.).

Langberg, Jonathan J., M.D., "Identification of ventricular tachycardia with use of the morphology of the endocardial electrogram," Circulation 77, No. 6, 1363-1369 (Jun. 1988).

Lindstrom, Ewa, et al., "Intracellular Calcium Oscillations in a T-Cell Line After Exposure to Extremely-Low-Frequency Magnetic Fields With Variable Frequencies and Flux Densities," Bioelectromagnetics, 16:41-47 (1995) (Copyright 1995 Wiley-Liss, Inc.).

Lorente P, Delgado C, Delmar M, Henzel D, Jalife J., "Hysteresis in the Excitability of Isolated Guinea Pig Ventricular Myocytes," Circ Res. Nov. 1991;69(5):1301-15.

Mercando, A. D., et al., "Automated Detection of Tachycardias by Antitachycardia Devices," Chapter 100, 943.

Palti, Yoram, et al., "Islets of Langerhans Generate Wavelike Electric Activity Modulated by Glucose Concentration," Diabetes, 45:595-601 (1996).

Paul, V. E., et al., "Automatic Recognition of Ventricular Arrhythmias Using Temporal Electrogram Analysis," PACE, vol. 14, 1265 (Aug. 1991).

Pumir, Alain, et al., "Control of rotating waves in cardiac muscle: analysis of the effect of an electric field," Proc R Soc Lond., 257: 129-134 (1994).

Ravazzi et al., Changes Induced in Ventricular Activator Using Non-Standard Pacing Pulse Morphologies at Different Right Septal Sites (1998).

Saihara S., Inoue H., Toda I., Usui M., Sugimoto T. "Summation of Excitation with a Single Conditioning Stimulus in the Canine Heart," Pacing Clin Electrophysiol. Jan. 1990; 13(1):52-8.

Sakuma, Ichiro, et al., "A Model Analysis of Aftereffects of High-Intensity DC Stimulation on Action Potential of Ventricular Muscle," IEEE Transactions on Biomedical Engineering, vol. 45, No. 2 (Feb. 1998) (Copyright 1998 IEEE).

Schirra, J., et al., "Mechanisms of the antidiabetic action of subcutaneous glucagon-like peptide-1(7-36) amide in non-insulin dependent diabetes mellitus," Journal of Endocrinology, 156, 177-186 (1998) (Copyright 1998 Journal of Endocrinology Ltd.).

Skale, Brian T., M.D., et al., "Inhibition of Premature Ventricular Extrastimuli by Subthreshold Conditioning Stimuli," J Am Coll Cardiol., 6:133-40 (1985).

Soria, B. and F. Martin, "Cytosolic Calcium Oscillations and Insulin Release in Pancreatic Islets of Langerhans," Diabetes & Metabolism (Paris), 24:37-40 (1998).

Stix, Guenter, et al. "Chronic electrical stimulation during the absolute refractory period of the myocardium improves severe heart failure." European Heart Journal (2004) 25, 650-655 (Elsevier Ltd. on behalf of European Society of Cardiology).

Sweeney, Robert J., et al., "Countershock Strength—Duration Relationship for Myocardial Refractory Period Extension," Acad. Emerg. Med., 2:57-62 (1995).

Sweeney, Robert J., Ph.D., et al., "Refractory Interval After Transcardiac Shocks During Ventricular Fibrillation," Circulation, 94:2947-2952 (1996) (Copyright 1996 American Heart Association, Inc.).

Sweeney, Robert J., Ph.D., et al., "Ventricular Refractory Period Extension Caused by Defibrillation Shocks," Circulation, 82:965-972 (1990).

Swerdlow, Charles D., M.D., et al., "Cardiovascular Collapse Caused by Electrocardiographically Silent 60-Hz Intracardiac Leakage Current, Implications for Electrical Safety," Circulation, 99:2559-2564 (1999) (Copyright 1999 American Heart Association, Inc.).

Talit, Uzi, et al., "The Effect of External Cardiac Pacing on Stroke Volume," PACE, vol. 13, 598 (May 1990).

Taniguchi, Akihiko, et al., "Inhomogeneity of cellular activation time and Vmax in normal myocardial tissue under electrical field stimulation," Am J Physiol. 267, H694-H705 (1994) (Copyright 1994 American Physiological Society).

Thakor, Nitish V., Ph.D., et al., "Effect of Varying Pacing Waveform Shapes on Propagation and Hemodynamics in the Rabbit Heart," Am J Cardiol., 79(6A): 36-43 (1997) (Copyright 1997 Excerpia Medica, Inc.).

Todd, Jeannie F., et al., "Subcutaneous glucagon-like peptide-1 improves postprandial glycaemic control over a 3-week period in patients with early Type 2 diabetes," Clinical Science, 95, 325-329 (1998) (Copyright 1998 The Biochemical Society and the Medical Research Society).

Tsong, Tian Y., "Electroporation of cell membranes," Biophys J, vol. 60, 297-306 (Aug. 1991).

Wessale, Jerry L., et al., "Stroke Volume and the Three Phase Cardiac Output Rate Relationship with Ventricular Pacing," PACE, vol. 13, 673 (May 1990).

Willems, Rik; Sipido, Karin R. "Nonexcitatory stimulation as a novel treatment for heart failure: cause for excitement?" European Heart Journal (2004) 25, 626-628 (Elsevier Ltd. on behalf of European Society of Cardiology).

Wirtzfeld, A., et al., "Physiology Pacing: Present Status and Future Developments," PACE, vol. 10, pt. I, 41 (Jan.-Feb. 1987).

Xue, Qiuzhen, et al., "Neural-Network-Based Adaptive Matched Filtering for QRS Detection," IEEE Transactions on Biomedical Engineering, vol. 39, No. 4 (Apr. 1992) (Copyright 1992 IEEE).

Yokoyama, Masayoshi, M.D., "The Phase of Supernormal Excitation in Relation to the Strength of Subthreshold Stimuli," Heart Institute of Japan, Tokyo Women's Medical College, 315 (Jun. 19, 1975).

Zilberter Yi, Starmer CF, Grant AO. "Open Na+ Channel Blockade: Multiple Rest States Revealed by Channel Interactions with Disopyramide and Quinidine," Am J Physiol. May 1994;266(5 pt 2):H2007-17.

* cited by examiner

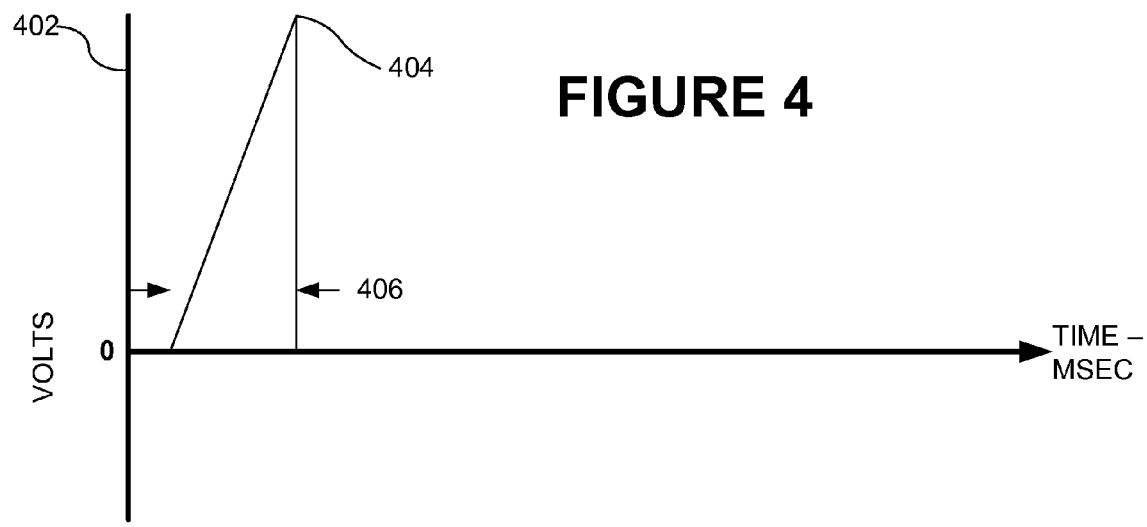
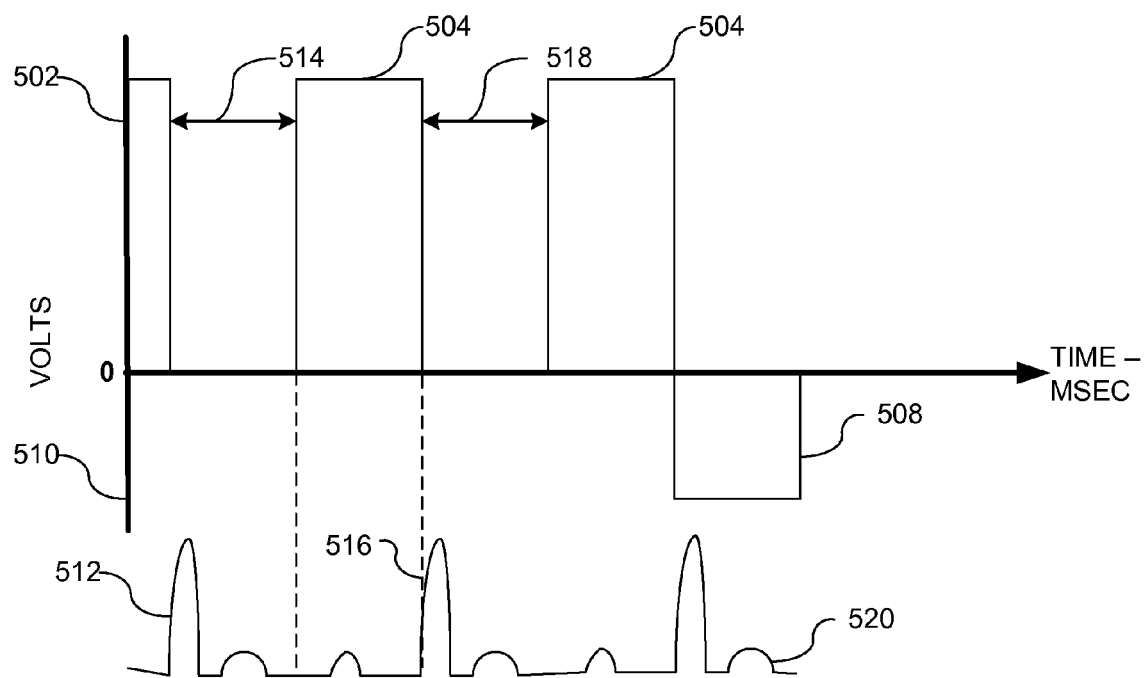

FIGURE 6

STEADY STATE VALUES

|          | Pmax | SEP | EDP  | EDV   | SW   |
|----------|------|-----|------|-------|------|
| Sinus    | 87.3 | 646 | 8.07 | 118   | 1650 |
| Cathodal | 84.9 | 551 | 8.3  | 118.9 | 1672 |
| Biphasic | 75.6 | 471 | 4.76 | 109.3 | 1034 |

All biphasic v. cathode differences significant at $p<.0.001$

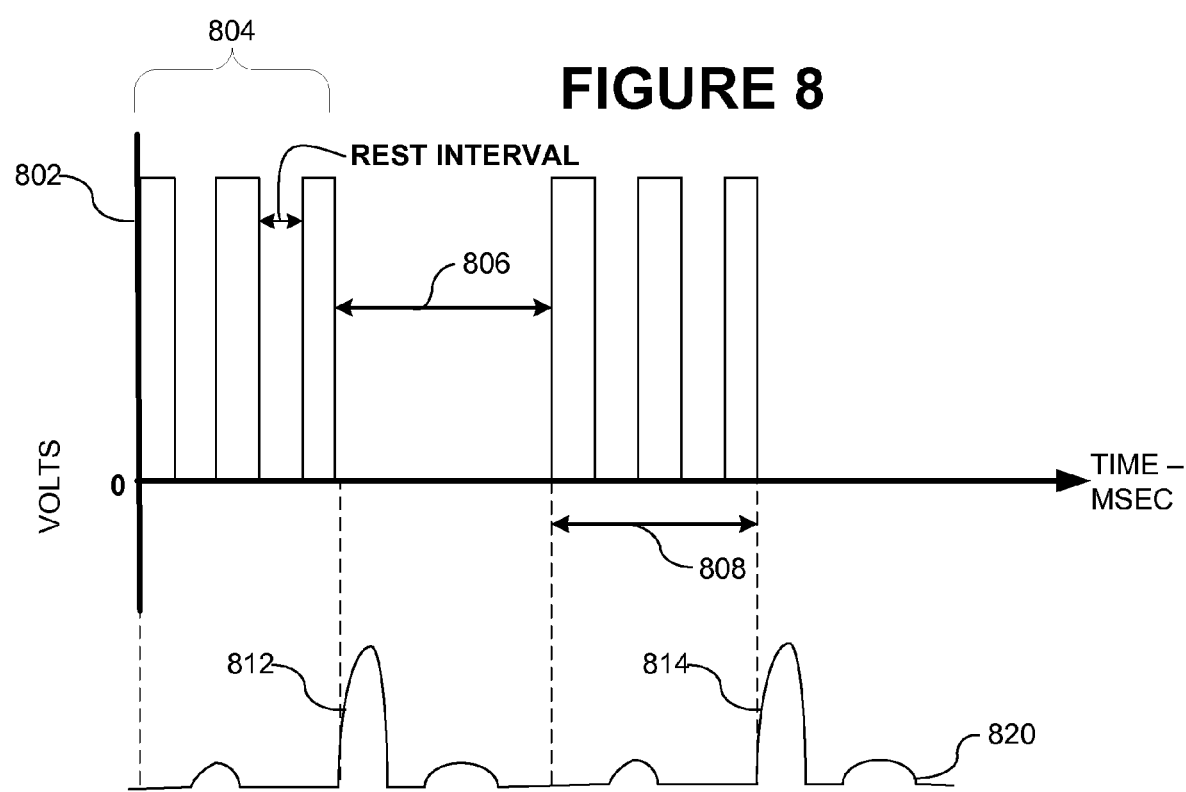

SYSTEM AND METHOD FOR TREATING ISCHEMIA BY IMPROVING CARDIAC EFFICIENCY

CROSS REFERENCE TO RELATED APPLICATIONS

This application claims the benefit under 35 U.S.C. §119 (e) of provisional application No. 60/814,734, filed Jun. 19, 2006 and is a continuation in part of U.S. application Ser. No. 11/731,203 filed Mar. 30, 2007, pending, which is a continuation of U.S. patent application Ser. No. 10/754,887 filed Jan. 10, 2004, now U.S. Pat. No. 7,203,537, which is a continuation-in-part of U.S. patent application Ser. No. 09/929,478 filed Aug. 14, 2001, now U.S. Pat. No. 6,895,274, which is a continuation of U.S. Ser. No. 09/231,570 application filed Jan. 14, 1999, now U.S. Pat. No. 6,295,470, which is a continuation-in-part of U.S. patent application Ser. No. 08/699,552, filed Aug. 19, 1996, now U.S. Pat. No. 5,871,506 and is related to U.S. patent application Ser. No. 11/141,403 filed May 31, 2005, which is a continuation-in-part of U.S. patent application Ser. No. 10/053,750, filed Jan. 21, 2002, pending, which is a continuation of U.S. patent application Ser. No. 09/690,947, filed Oct. 18, 2000, now U.S. Pat. No. 6,341,235, which is a continuation-in-part of U.S. patent application Ser. No. 09/008,636 filed Jan. 16, 1998, now U.S. Pat. No. 6,136,019, which is a continuation-in-part of U.S. patent application Ser. No. 08/699,552, filed Aug. 19, 1996, now U.S. Pat. No. 5,871,506. The Ser. Nos. 60/814,734, 11/731,203, 10/754,887, 09/929,478, 09/231,570, 11/141,403, 10/053,750, 09/690,947, 09/008,636, and 08/699,552 applications are all incorporated by reference herein, in their entirety, for all purposes.

BACKGROUND AND SUMMARY

In physics, work is the product of a force and a distance. Therefore, considering a solid object of a given mass, the work done to move the object is the force applied to the object times the distance that the object moves. In the case of the work done to move a volume of fluid, work is defined as the product of the volume of fluid and the pressure required to move the fluid. Stroke work (SW) refers to the work done by the ventricle to eject a volume of blood (i.e., stroke volume) into the aorta. The force that is applied to the volume of blood is the intraventricular pressure.

The interplay between ventricular function (including both ventricular filling and ejection) and the circulation can be seen when ventricular pressure is plotted against ventricular pressure at various points in time. FIG. 1 illustrates a pressure volume loop 100 as known in the art. The pressure volume loop 100 reflects the cardiac cycle of ventricular filling (a), isovolumetric contraction (b), ventricular ejection (c) and isovolumetric relaxation (d).

The end-diastolic volume (EDV) 130 is the maximum volume achieved at the end of filling, and end-systolic volume (ESV) 140 is the minimal volume (i.e., residual volume) of the ventricle found at the end of ejection. The width of the loop, therefore, represents the difference between EDV and ESV, which is by definition the stroke volume 110 (SV). The cardiac cycle, and the work performed by the heart, is confined within boundaries that define this interaction at end-diastole (the end-diastolic pressure-volume relationship or EDPVR 120) and at end-systole (the end-systolic pressure volume relationship or ESPVR 115). The ESPVR 115 is the maximum pressure at any given left ventricular volume that can be developed by the ventricle and represents the inotropic state of the ventricle. The slope of the ESPVR 115 is independent of ventricular loading and is a measure of the inherent contractility of the ventricle at that time.

The area of the pressure-volume loop 110 represents stroke work, which is the work of the heart each heart beat. While prior art pacing devices are focused on increasing cardiac output, the long term health of the cardiac patient would be improved by techniques that reduce the work required to eject a given volume of blood during a heart beat thereby increasing cardiac efficiency.

Ischemia is an oxygen starvation of the myocardium that is a precursor to myocardial infarction or the death of the starved myocardial cells. Angina pectoris is chest pain brought on by ischemic myocardial tissue. The pain comes approximately when the demand of the heart muscle for oxygen exceeds the ability of the coronary arteries to deliver it. The amount of oxygen extracted by the heart muscle in order to produce useful heart muscle contraction is related to the amount of work the heart muscle has to do, and more especially on the pressure against which the heart has to pump the blood. Thus, on exercise, more work is done and more oxygen required. Heart rate and blood pressure typically rise to try to help supply the need. If the myocardium is made more efficient, i.e. able to develop the needed hemodynamics with less work, the threshold for development of chest pain will be raised, and the patient will be better able to exercise.

It would be useful to provide a method of reducing ischemia by reducing the stroke work of the ventricles.

DESCRIPTION OF THE FIGURES

FIG. 4 is a schematic representation of ramped anodal pulse according to an embodiment hereof.

FIG. 5 is a schematic representation of a series of anodal pulses followed by a cathodal pulse according to an embodiment hereof.

FIG. 6 presents test data relating the effects of differing waveforms on stroke work.

FIG. 8 illustrates an anodal waveform comprising multiple anodal pulses according to an embodiment hereof.

DETAILED DESCRIPTION

In an embodiment, ischemic heart disease is treated by increasing heart efficiency. In this embodiment, the efficiency of the heart is improved by increasing the resting membrane potential of the myocardial cells, increasing the size of the anodal virtual stimulatory electrode, or reducing the ventricular stretching during filling of the ventricle.

In an embodiment, a pacing lead is attached to the right ventricle. Alternatively, the pacing lead may be situated in the blood pool of the right ventricle. An anodal pulse is applied to heart prior to cardiac depolarization.

Figure 2:
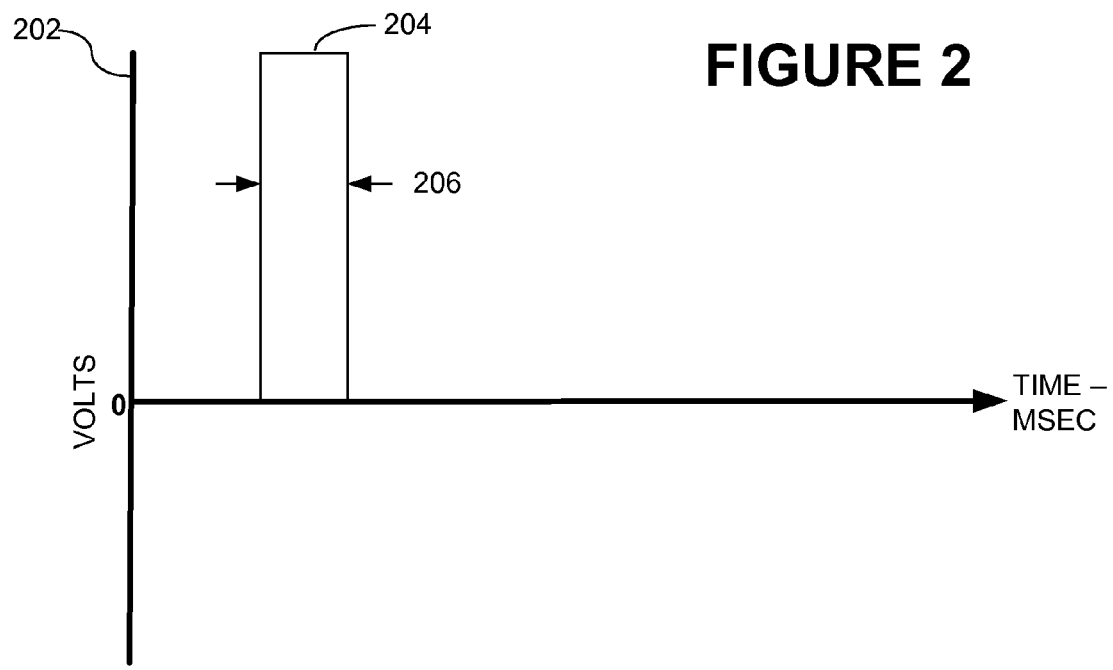
FIG. 2 is a schematic representation of an anodal pulse according to an embodiment hereof.

FIG. 2 is a schematic representation of an anodal pulse 204 according to an embodiment hereof. The amplitude 202 of the anodal pulse 204 is at or above the stimulation threshold and may range from approximately 3 volts to approximately 20 volts. The width 206 of anodal pulse 202 may range from approximately 0.1 milliseconds to approximately 0.7 milliseconds. The heart of a patient with ischemia is paced directly with an anodal pulse, either constantly or only when ischemia is detected.

Figure 7:
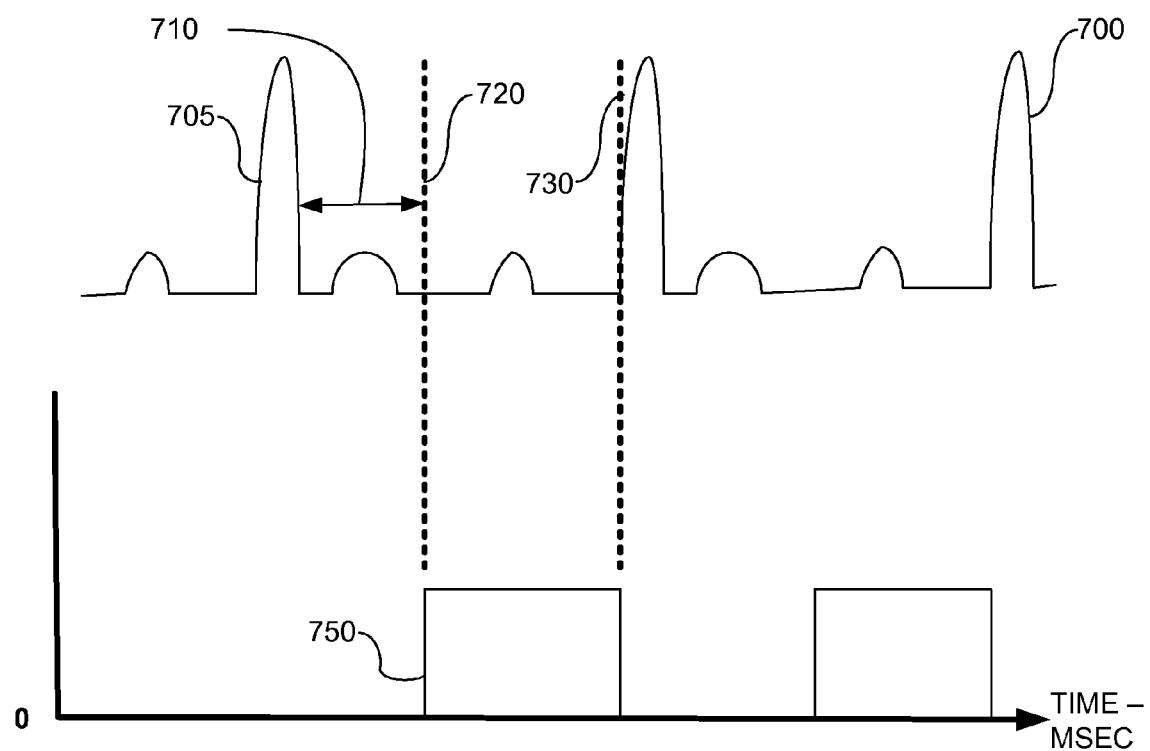
FIG. 7 illustrates the application of an anodal pulse relative to the electrogram of a heartbeat according to an embodiment hereof.

FIG. 7 illustrates the application of an anodal pulse 750 relative to the electrogram 700 of a cardiac cycle according to an embodiment hereof. A heartbeat 705 is detected. After a delay period 710, the anodal pulse 750 is applied to the heart at 720. The duration of the pulse is determined by the detection of a subsequent heart beat 730, at which time the anodal pulse 750 is discontinued. Typically, the delay period is approximately 200-400 milliseconds. In an embodiment of the present invention, sensing is used to vary the timing between the ventricular depolarization event 720 and the timing of the application of the anodal pulse 750.

The timing of the application of the anodal pulse relative to the heartbeat as illustrated in FIG. 7 may be utilized in either a direct pacing regime where measures of ischemia are not detected or where the determination to apply the anodal pulse is based on sensed measures of ischemia.

Figure 3:
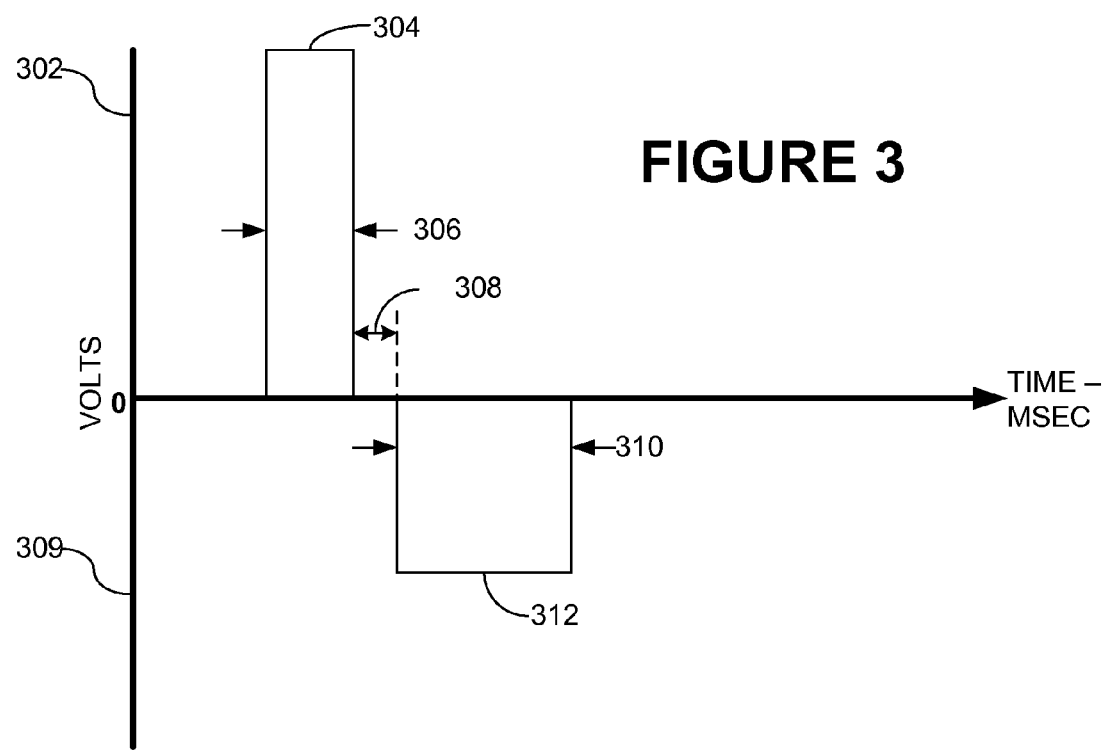
FIG. 3 is a schematic representation of a biphasic waveform according to another embodiment hereof.

The application of an anodal stimulation pulse can result in an increasing stimulation threshold. FIG. 3 is a schematic representation of a biphasic waveform comprising an anodal pulse 304 and a cathodal pulse 312 according to an embodiment hereof. The anodal pulse 304 is followed by a cathodal pulse 312 to obviate the increase in the anodal stimulation threshold. The amplitude 302 of the anodal pulse 304 is at or above the stimulation threshold and may range from approximately 3 Volts to approximately 20 Volts. The width 306 of the anodal pulse 303 may range from approximately 0.1 milliseconds to approximately 0.7 milliseconds. The amplitude 309 of the cathodal pulse 312 may range from approximately 4-6 Volts. The width 310 of the cathodal pulse 312 may range from 0.3 to 1 millisecond. The interpulse interval 308 may range from 0 to approximately 0.25 milliseconds.

FIG. 4 is a schematic representation of ramped anodal pulse 404 according to an embodiment hereof. In this embodiment, the anodal pulse 404 waveform is ramped to amplitude 402 while retaining the pulse width 406. The ramp of rising amplitude may be linear or non-linear, and the slope may vary.

FIG. 5 is a schematic representation of the application of a series anodal pulses 504 relative to an electrogram 520 of a cardiac cycle according to an embodiment hereof. A heartbeat 512 is detected. After a delay period 514, an anodal pulse 504 is applied to the heart. The duration of the pulse is determined by the detection of a subsequent heart beat 516, at which time the anodal pulse is discontinued. Following a second delay 518, another anodal pulse 504 is applied to the heart. After either a preset number of anodal pulses or a preset number of heartbeats, a cathodal pulse 508 is applied to the heart to obviate the increase in the anodal stimulation threshold.

Again, the timing of the application of the anodal pulse relative to the heartbeat as illustrated in FIG. 5 may be utilized in either a direct pacing regime where measures of ischemia are not detected or where the determination to apply the anodal pulse is based on sensed measures of ischemia.

FIG. 8 is a schematic representation of the application of a series anodal pulses 804 applied during a single heartbeat interval (interval defined by 812-814) relative to an electrogram 820 of a cardiac cycle. A heartbeat 812 is detected. After a delay period 806, a series of anodal pulses 804 is applied to the heart. The duration of the series of anodal pulses 804 is determined by the detection of a subsequent heart beat 814, at which time the series of anodal pulses 804 is discontinued. Following a second delay period (not illustrated), another anodal series of anodal pulses is applied to the heart Again, the timing of the application of the anodal pulse relative to the heartbeat as illustrated in FIG. 8 may be utilized in either a direct pacing regime where measures of ischemia are not detected or where the determination to apply the anodal pulse is based on sensed measures of ischemia. The individual pulses of the series of pulses may be square waves, or they may be of any other shape, for example, pulses which decay linearly or curvilinearly from an initial amplitude to a lower amplitude.

As previously described, the series of anodal pulses may be followed by a cathodal pulse.

In the embodiments described above, the application of the anodal pulse results in an increase in the slope of the upstroke of the action potential, an increase in sodium influx (along with calcium), and an augmentation of contraction albeit at lower peak pressure and ventricular volumes. Because oxygen demand is related to pressure, volume, and heart rate, this enables more oxygen to be delivered at no extra metabolic cost.

In an embodiment, an anodal pulse is applied to the cardiac tissue in response to the sensing of ischemia. For example, a sensor monitors an ST segment depression on a ventricular sensing (pacing) lead, a pH change, a lactate buildup, or other suitable change which occurs when ischemia is present. The therapy may also be triggered by the patient in response to ischemic chest pain symptoms.

In another embodiment of the present invention, sensing is used to adjust the timing of the application of the anodal pulse. In this embodiment, pacing of the RV with the anodal pulse is rate sensitive. By way of illustration and not as a limitation, sensing may be directed to physiological parameters, as for example, central venous blood temperature, blood pH level, QT time interval and respiration rate. Alternatively, sensing may be directed to measures of physical activity that relate to a patient's metabolic need.

Figure 1:
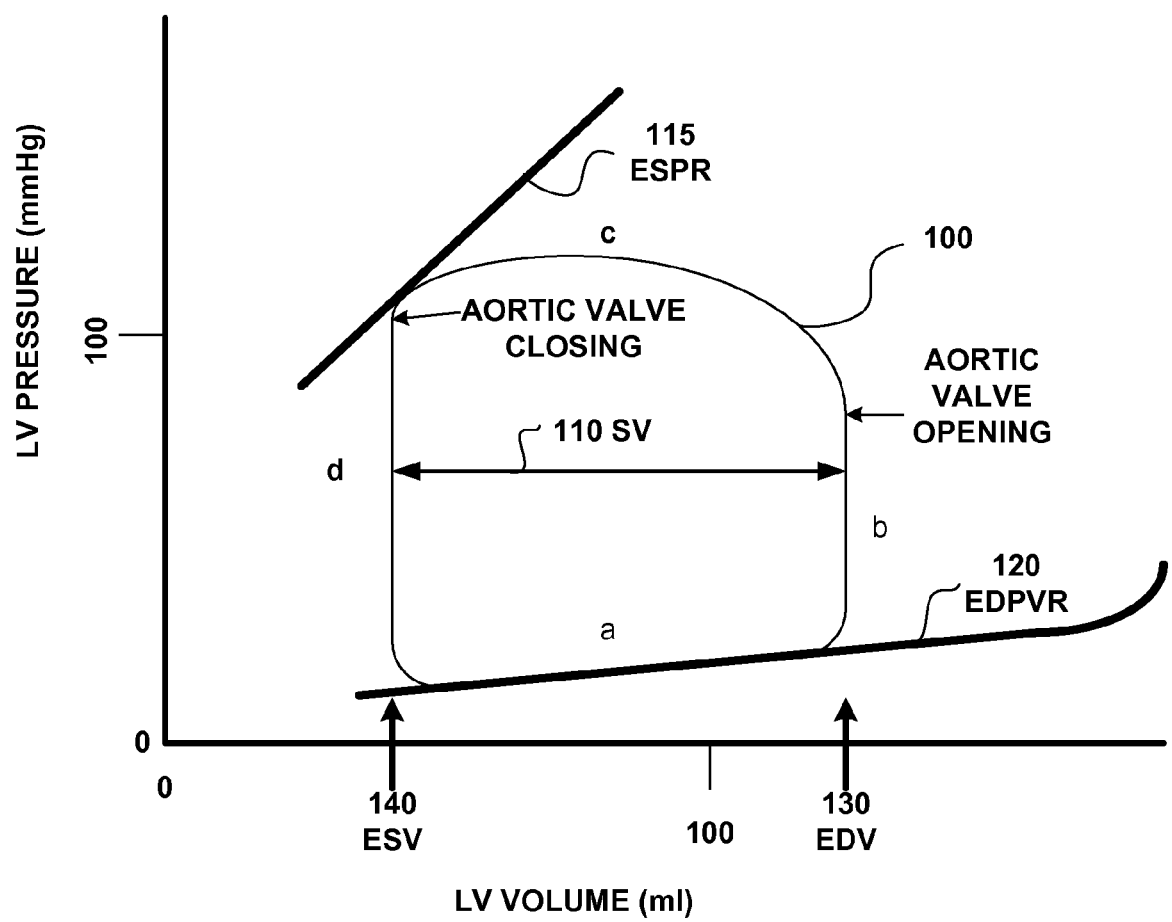
FIG. 1 illustrates a pressure-volume loop as known in the art.

A study of myocardial contractility in swine using pressure-volume loops was performed. (A discussion of pressure-volume loops is provided above; see also FIG. 1.) Data from this study are presented in FIG. 6. The area enclosed by the loops is referred to as the stroke work (see, FIG. 1), which is the work that the heart has to do to produce the hemodynamics noted for that particular beat. The data presented in FIG. 6 illustrates that a waveform comprising an anodal pulse followed by a cathodal pulse results in paced beats having stroke work markedly smaller than cathodal pulses (1034 v. 1672) at the same paced heart rate and sinus at a slightly slower heart rate (1034 v. 1650). As indicated by these data, a biphasic pulse having a leading anodal phase is the most efficient.

As noted, ischemia is the inability of the heart to receive sufficient oxygen. Although myocardial oxygen consumption can be measured directly by assessing the difference between aortic root and coronary sinus oxygen content multiplied by heart rate, another surrogate measurement that is proportional to myocardial oxygen consumption which can be measured even more easily is the peak pressure-rate product. In the case of the data presented in FIG. 7, Pmax is 75.6 vs 84.9 and 87.3 for biphasic, cathodal, and sinus, at heart rates of 113, 113, and 105 respectively. The respective pressure-rate products are 8,542.8 (biphasic), 9,593.7 (cathodal), and 9,166.5 (sinus). Thus, a biphasic waveform having a large anodal leading phase is again the most efficient.

It has been demonstrated that the blood pressure following an anodal stimulation shows lower systolic and higher diastolic than the cathodal stimulation. The former is a good measure for the work that the heart has to do pumping against the systemic resistance. Also since coronary blood flow occurs during diastole, the higher diastolic pressure means better coronary perfusion with anodal.

Referring again to FIG. 1, the total area under the curve is proportional to myocardial O2 demand. Data indicate that the O2 demand is appreciably smaller for the anodal stimulation than for cathodal stimulation.

In response to a stimulatory anodal pulse, the left ventricle pressure curve is altered favorably, and so is the volume signal resulting from a decreased compliance.

In an embodiment, a cardiac stimulator comprises a cardiac sensor, a processor, a waveform generator and an electrode. The cardiac sensor that senses a measure of heart function. The cardiac sensor produces an output signal indicative of the heart function measure. By way of illustration and not as a limitation, the measure indicative of ischemia is selected from the group consisting of an ST segment depression on a ventricular sensing (pacing) lead, a pH change, and a lactate buildup. The processor comprises instructions for producing a first alert signal if the heart function measure is indicative of ischemia. The waveform generator produces a stimulation signal in response to the first alert signal. The stimulation signal comprises an anodal phase having an amplitude and a duration greater than or equal to the diastolic depolarization threshold. By way of illustration and not as a limitation, the anodal phase amplitude is about 3-20 volts and the anodal pulse with about 0.1-0.7 milliseconds.

The electrode applies the stimulation signal to the cardiac tissue.

In an embodiment, the waveform generator further produces a cathodal phase in response to the alert signal. In this embodiment, the stimulation signal comprises the anodal phase and the cathodal phase. The cathodal phase follows the anodal phase after a delay of from 0 to about 0.25 milliseconds.

In another embodiment, the waveform generator further produces a cathodal phase after a preset number of anodal phases. In this embodiment, the stimulation signal comprises the anodal phase and the cathodal phase. The cathodal phase follows the anodal phase after a delay of from 0 to about 0.25 milliseconds.

In another embodiment, the processor further comprises instructions for detecting a preset number of heartbeats and for issuing a second alert signal when the preset number of heartbeats is reached. In this embodiment, the waveform generator further produces a cathodal phase in response to the second alert signal. The stimulation signal comprises the anodal phase and the cathodal phase. The cathodal phase follows the anodal phase after a delay of from 0 to about 0.25 milliseconds.

In another embodiment, the cardiac stimulator further comprises a user interface. The user interface comprises instructions for accepting a demand signal from a user of the cardiac stimulator and sending the demand signal to the processor. The processor further comprises instructions for producing the first alert signal from the demand signal.

It will be understood that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular. The waveforms illustrated in the figures are not to scale.

What is claimed is:

1. A cardiac stimulator comprising:
   a cardiac sensor, wherein the cardiac sensor senses a measure of heart function and wherein the cardiac sensor produces an output signal indicative of the heart function measure;
   a processor, wherein the processor comprises instructions for producing a first alert signal if the heart function measure is indicative of ischemia;
   a waveform generator, wherein the waveform generator produces a stimulation signal in response to the first alert signal and wherein the stimulation signal comprises a leading anodal phase and a trailing phase cathodal phase that is produced after two or more leading anodal phases and wherein the trailing phase follows a preceding leading anodal phase after a delay of from 0 to about 0.25 milliseconds;
   and
   an electrode for applying the stimulation signal to the cardiac tissue.

2. The cardiac stimulator of claim 1, wherein the measure indicative of ischemia is selected from the group consisting of an ST segment depression on a ventricular sensing (pacing) lead, a pH change, and a lactate buildup.

3. The cardiac stimulator of claim 1, wherein the leading anodal phase amplitude is about 3-20 volts.

4. The cardiac stimulator of claim 1, wherein the leading anodal phase width is about 0.1 milliseconds to 0.7 milliseconds.

5. The cardiac stimulator of claim 1, wherein the trailing phase is a cathodal phase that follows the leading anodal phase after a delay of from 0 to about 0.25 milliseconds.

6. The cardiac stimulator of claim 1,
   wherein the processor further comprises instructions for:
   detecting a preset number of heartbeats; and
   issuing a second alert signal when the preset number of heartbeats is reached,
   wherein the trailing phase is a cathodal phase produced in response to the second alert signal.

7. The cardiac stimulator of claim 1 further comprising a user interface, wherein the user interface comprises instructions for:
   accepting a demand signal from a user of the cardiac stimulator; and
   sending the demand signal to the processor, and
   wherein the processor further comprises instructions for producing the first alert signal from the demand signal.

8. A cardiac stimulator comprising:
   a cardiac sensor, wherein the cardiac sensor senses a measure of heart function and wherein the cardiac sensor produces an output signal indicative of the heart function measure;
   a processor, wherein the processor comprises instructions for producing a first alert signal if the heart function measure is indicative of ischemia;
   a waveform generator, wherein the waveform generator produces a stimulation signal solely comprising an anodal waveform in response to the first alert signal and wherein the stimulation signal has an amplitude and a duration; and
   an electrode for applying the stimulation signal to the cardiac tissue.

9. The cardiac stimulator of claim 8, wherein the measure indicative of ischemia is selected from the group consisting of an ST segment depression on a ventricular sensing (pacing) lead, a pH change, and a lactate buildup.

10. The cardiac stimulator of claim 8, wherein the amplitude is about 3-20 volts.

11. The cardiac stimulator of claim 8, wherein the duration is about 0.1 milliseconds to 0.7 milliseconds.

* * * * *